(12) United States Patent
Carpenter et al.

(10) Patent No.: US 12,060,314 B2
(45) Date of Patent: Aug. 13, 2024

(54) BRANCHED ALCOHOLS FORMED FROM VINYLIDENE OLEFINS BY HYDROFORMYLATION AND METHODS FOR PRODUCTION THEREOF

(71) Applicant: ExxonMobil Chemical Patents Inc., Baytown, TX (US)

(72) Inventors: Alex E Carpenter, Houston, TX (US); Sarah J Mattler, League City, TX (US); Danielle G. Singleton, Houston, TX (US); Jennifer L. Rapp, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 318 days.

(21) Appl. No.: 17/596,246

(22) PCT Filed: Jun. 15, 2020

(86) PCT No.: PCT/US2020/037730
§ 371 (c)(1),
(2) Date: Dec. 6, 2021

(87) PCT Pub. No.: WO2020/257100
PCT Pub. Date: Dec. 24, 2020

(65) Prior Publication Data
US 2022/0306558 A1 Sep. 29, 2022

Related U.S. Application Data

(60) Provisional application No. 62/864,328, filed on Jun. 20, 2019.

(30) Foreign Application Priority Data

Oct. 11, 2019 (EP) ..................... 19202776

(51) Int. Cl.
*C07C 29/141* (2006.01)
*C07C 29/80* (2006.01)
*C07C 45/50* (2006.01)

(52) U.S. Cl.
CPC ............ *C07C 29/141* (2013.01); *C07C 29/80* (2013.01); *C07C 45/505* (2013.01)

(58) Field of Classification Search
CPC ...... C07C 29/141; C07C 29/80; C07C 45/505
See application file for complete search history.

(56) References Cited

U.S. PATENT DOCUMENTS

| | | | |
|---|---|---|---|
| 3,952,068 A | 4/1976 | Gipson et al. | |
| 2018/0282359 A1 | 10/2018 | Crowther et al. | |

FOREIGN PATENT DOCUMENTS

| | | |
|---|---|---|
| GB | 2 451 325 | 1/2009 |
| WO | WO 1997/00843 | 1/1997 |
| WO | WO 2001/30736 | 5/2001 |
| WO | WO 2019/045809 | 3/2019 |

*Primary Examiner* — Sikarl A Witherspoon (57) ABSTRACT

Vinylidene olefins may undergo hydroformylation in the presence of an unmodified cobalt catalyst to form compositions comprising a mixture of alcohol molecules having a specified amount of branching. In particular, the compositions may feature a mixture comprising reduced hydroformylated reaction products of a vinylidene olefin comprising alcohol molecules represented by at least one of Structures 3-5. The mixture has an average of about 1.2 to about 2.1 branches per alcohol molecule. $R^a$ and $R^b$ may be the same or different and comprise a branched or unbranched alkyl group having about 6 to about 14 carbon atoms, excluding branches. Variable m is an integer ranging from 0 to a number of carbon atoms in $R^b$. $R^{b'}$ is a branched or unbranched alkyl group having m+1 carbon atoms less than $R^b$.

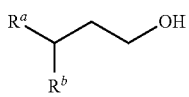

Structure 3

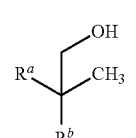

Structure 4

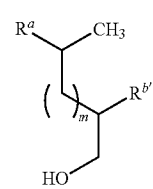

Structure 5

25 Claims, 3 Drawing Sheets

BRANCHED ALCOHOLS FORMED FROM VINYLIDENE OLEFINS BY HYDROFORMYLATION AND METHODS FOR PRODUCTION THEREOF

CLAIM TO PRIORITY

This application is a National Phase Application claiming priority to PCT Application Serial No. PCT/US2020/037730 filed Jun. 15, 2020, which claims priority to U.S. Provisional Application No. 62/864,328 filed Jun. 20, 2019, and European Patent Application No. 19202776.1, which was filed Oct. 11, 2019, the disclosures of which are incorporated herein by reference in their entireties.

BACKGROUND

Long-chain alcohols or functionalized products formed therefrom may find utility in a number of applications due to their amphiphilic character. In non-limiting examples, long-chain alcohols or functionalized products formed therefrom may find use as surfactants, emollients, lubricants, coatings, wetting agents, corrosion inhibitors, synthetic base stocks, and/or therapeutic delivery agents.

Long-chain alcohols may be prepared from a starting material having a substantially linear carbon chain with limited branching, such as a linear alpha olefin or linear alpha olefin oligomer bearing vinyl termination of the carbon chain. Conversion of the vinyl olefin moiety into an alcohol moiety oftentimes preserves the linearity of the carbon chain without introducing chain branches and results in the alcohol moiety being located at or near the terminus of the carbon chain. Reduction of naturally occurring fatty acids may likewise afford long-chain alcohols having similar structural features.

There are comparatively few methods for preparing long-chain alcohols having a controlled degree of branching, particularly with the alcohol moiety being introduced remote from the terminus of the carbon chain (e.g., upon the terminal carbon atom or the first non-terminal carbon atom of the carbon chain). One example route for producing branched long-chain alcohols is the Guerbet reaction, wherein the alcohol moiety may reside deep within the interior of the carbon chain. In the Guerbet reaction, two primary alcohols may undergo condensation to form a branched long-chain alcohol condensation product bearing a tertiary carbon atom branch located at the β-position with respect to the alcohol moiety. Other than changing the alcohol(s) undergoing condensation, there is little opportunity for varying the branch position or the location of the alcohol moiety in the condensation product. Hydroformylation is another route commonly used for producing long-chain alcohols from vinyl-terminated olefins, such as the Shell Higher Olefin Process (SHOP). When hydroformylating vinyl-terminated olefins, branching, if present at all, is located near the terminus of the carbon chain, leaving the branches rather short as a result. Hydroformylation of vinyl-terminated olefins also usually introduces the alcohol moiety at or near the terminus of the carbon chain.

At present, there is limited opportunity for accessing more structurally diverse long-chain alcohols having a controlled number of relatively long branches for use in applications where other long-chain alcohols may be ineffective or perform poorly. There is similarly limited access to long-chain alcohols having the alcohol moiety located more deeply within the interior of the carbon chain to address presently unmet or unknown application-specific needs within various industries. Changing the molecular shape of a long-chain alcohol in one or both of these manners may alter one or more of melting point, solubility, or emulsifying behavior, as non-limiting examples, to address various application-specific needs.

SUMMARY

Compositions described herein may comprise: a mixture comprising reduced hydroformylated reaction products of a vinylidene olefin. The reduced hydroformylated reaction products of the vinylidene olefin comprise alcohol molecules represented by at least one of Structure 3, Structure 4, and Structure 5.

The mixture has an average of about 1.2 to about 2.1 branches per alcohol molecule. $R^a$ and $R^b$ are each a branched or unbranched alkyl group having about 6 to about 14 carbon atoms, excluding branches and $R^a$ and $R^b$ are the same or different. Variable m is an integer ranging from 0 to a number of carbon atoms in $R^b$. $R^{b'}$ is a branched or unbranched alkyl group having m+1 carbon atoms less than $R^b$.

Methods of the present disclosure may comprise: providing an olefin feed comprising a vinylidene olefin represented by Structure 1, contacting the olefin feed with a syngas mixture comprising carbon monoxide and hydrogen in the presence of an unmodified cobalt catalyst to form hydroformylated reaction products of the vinylidene olefin, and reducing the hydroformylated reaction products of the vinylidene olefin to form a mixture comprising reduced hydroformylated reaction products of the vinylidene olefin. The reduced hydroformylated reaction products of the vinylidene olefin comprise alcohol molecules represented by at least one of Structure 3, Structure 4, and Structure 5.

The mixture has an average of about 1.2 to about 2.1 branches per alcohol molecule. $R^a$ and $R^b$ are each a branched or unbranched alkyl group having about 6 to about 14 carbon atoms, excluding branches and $R^a$ and $R^b$ are the same or different. Variable m is an integer ranging from 0 to a number of carbon atoms in $R^b$. $R^{b'}$ is a branched or unbranched alkyl group having m+1 carbon atoms less than $R^b$.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, as will occur to one of ordinary skill in the art and having the benefit of this disclosure.

DETAILED DESCRIPTION

The present disclosure generally relates to long-chain alcohols and, more specifically, to long-chain alcohols obtained through hydroformylation of olefin compositions containing variable amounts of a vinylidene olefin and optionally a vinylene olefin such that a controlled extent of chain branching occurs.

As discussed above, there is limited structural diversity available when synthesizing long-chain alcohols using presently available methods. Current synthetic methods may afford long-chain alcohols having very limited or no branching, and the branches that are present may be rather short by virtue of their proximity to the terminus of the carbon chain. In addition, the alcohol moiety may be introduced at or near the terminus of the carbon chain. Substantially linear alcohol molecules of these types may be unsuitable or non-optimal for some applications. Although certain branched long-chain alcohols may be prepared by the Guerbet reaction, there is limited opportunity to modify the branch position and/or branch length to meet various application-specific needs, such as melting point, solubility, and emulsifying behavior, for example.

The present disclosure provides ready access to a family of structurally related long-chain alcohols having branching that may be introduced in a controlled manner. In particular, the present disclosure demonstrates that vinylidene olefins may undergo controlled hydroformylation to introduce a hydroxymethyl (—CH$_2$OH) functionality, a primary alcohol moiety, in a manner such that β-branched alcohols are formed within a mixture instead of predominantly γ-branched alcohols, with the average number of branches in the mixture residing within a relatively narrow range. The β-branched alcohols bear two branches per alcohol molecule, absent side chain branching in the olefin starting material, whereas the γ-branched alcohols generally bear only a single branch. Thus, the average number of branches exhibited by the mixture is statistically weighted toward the two branches of the β-branched alcohols.

As used herein, the term "hydroformylation" refers to the combined process of introducing an aldehyde moiety to an olefin and subsequently reducing the aldehyde moiety to a primary alcohol moiety. For clarity of description and to distinguish between the two process operations herein, the non-reduced (aldehyde) reaction products may be referred to in the present disclosure as "hydroformylated reaction products" or "non-reduced hydroformylated reaction products" and the reduced (primary alcohol) reaction products may be referred to herein as "reduced hydroformylated reaction products."

More specifically, the present disclosure demonstrates that vinylidene olefins may undergo hydroformylation in the presence of an unmodified cobalt catalyst to afford a mixture comprising one or more branched long-chain alcohols (reduced hydroformylated reaction products), in which β-branched alcohols are formed in appreciable yields compared to γ-branched alcohols, in contrast to other types of hydroformylation processes. Based on their relative rates of formation, the mixture of γ-branched and β-branched alcohols may exhibit an average of about 1.2 branches per alcohol molecule up to about 2 branches per alcohol molecule, provided that no additional branches are present in the vinylidene olefin molecular structure prior to hydroformylation. The average number of branches may exceed the theoretical maximum of 2 if additional branches are present in the vinylidene olefin prior to hydroformylation and/or are introduced during hydroformylation. For example, the average number of branches may be up to about 2.1 branches per alcohol molecule in the present disclosure. Accordingly, the mixture of reduced hydroformylated reaction products produced according to the present disclosure may exhibit an average of about 1.2 to about 2.1 branches per alcohol molecule, or about 1.7 to about 2.1 branches per alcohol molecule, or about 1.2 to 2.0 branches per alcohol molecule. Ligand-modified hydroformylation catalysts (e.g., phosphine-modified catalysts), in contrast, tend to favor formation of γ-branched alcohols, thereby resulting in mixtures of reduced hydroformylated reaction products having a lower average number of branches.

β-Branched long-chain alcohols formed from a vinylidene olefin according to the disclosure herein feature both a methyl branch arising from the vinylidene group and one additional branch, provided that no additional branching was already present in the molecular structure of the vinylidene olefin. Although the methyl branch is short, the other branch may be much longer than in many other methods for forming branched long-chain alcohols. Moreover, the alcohol moiety introduced when hydroformylating a vinylidene olefin may reside considerably deeper within the carbon chain than is possible when hydroformylating a vinyl-terminated olefin, thereby providing another advantageous structural distinction.

Although any vinylidene olefin may undergo hydroformylation according to the disclosure herein, it may be advantageous if the vinylidene olefin is prepared by dimerizating a linear alpha olefin in the presence of a suitable metallocene catalyst. Linear alpha olefins are a readily available and inexpensive commercial feedstock having a range of carbon chain lengths (typically having an even number of carbon atoms), any of which may undergo ready dimerization to afford vinylidene olefins having variable placement of the vinylidene group. Dimerization of one or more linear alpha olefins may place the vinylidene group deep within the interior of the olefin molecule, thereby affording long chain branches and corresponding deep placement of the alcohol moiety once hydroformylation has taken place. Moreover, dimerization of two different linear alpha olefin molecules may alter the position of the vinylidene group within the carbon chain of the vinylidene olefin, thereby offering some degree of flexibility in where the alcohol moiety and chain branching resides following hydroformylation. For example, dimerization of 1-octene may place the vinylidene group at different location than does a mixture of 1-hexene and 1-decene, even though both feedstocks may produce a $C_{16}$ vinylidene olefin dimer. Thus, vinylidene olefins formed from linear alpha olefins offer considerable synthetic flexibility in addition to their other various advantages.

When dimerizing one or more linear alpha olefins using a metallocene catalyst, non-vinylidene disubstituted olefins and trisubstituted olefins are often produced as side reaction products in variable yields. Collectively, non-vinylidene disubstituted olefins and trisubstituted olefins are referred to herein as "vinylene olefins". The amount of non-vinylidene disubstituted olefins and/or trisubstituted olefins formed may depend up the metallocene catalyst and reaction conditions used. The trisubstituted olefins may similarly undergo hydroformylation in conjunction with the vinylidene olefins according to the disclosure herein to produce additional long-chain alcohols having further structural diversity. Advantageously, many of the long-chain alcohols formable from trisubstituted olefins may exhibit two chain branches (e.g., Structures 6-8 and 10 below), thereby contributing further to the average number of branches in the mixture. Disubstituted olefins, in contrast, may lead to long-chain alcohols having a single branch following hydroformylation. Thus, reduced hydroformylated reaction products formed from trisubstituted olefins may supplement (increase) the average number of branches formed in the product mixture. Accordingly, unless required for particular application-specific needs, the hydroformylated reaction products of the trisubstituted olefins may remain combined with those produced from the related vinylidene olefins. Advantageously, this avoids having to perform a difficult separation of isomeric molecules at the olefin, aldehyde or alcohol product stage. It is to be appreciated, of course, that the reduced hydroformylated reaction products of the trisubstituted olefins may be separated from those formed from vinylidene olefins, if needed, to address particular application-specific needs.

In addition to branched long-chain alcohols formed from vinylidene olefins and optionally vinylene olefins, the hydroformylation methods of the present disclosure may concurrently form various unfunctionalized saturated hydrocarbons. The unfunctionalized saturated hydrocarbons may arise from over-reduction of either the vinylidene and/or vinylene olefins or the hydroformylated reaction products derived therefrom. Advantageously, the unfunctionalized saturated hydrocarbons may remain within the mixture of branched long-chain alcohols without exerting significant impact upon their properties. If desired to address particular application-specific needs, however, the reduced hydroformylated reaction products formed according to the disclosure herein may be isolated, such as by vacuum distillation, to remove at least a portion of the unfunctionalized saturated hydrocarbons.

Accordingly, the present disclosure provides ready access to various long-chain alcohol compositions having a controlled extent of branching. The long-chain alcohols formed according to the disclosure herein may afford kinematic viscosity properties distinct from that obtainable from other olefin sources and other hydroformylation catalysts. The branched long-chain alcohols may also be structurally distinct from those formed through other routes, including the Guerbet reaction. The lubricant and viscosity properties may be conveniently tailored through control of the branch content, which may be regulated by selecting the chosen hydroformylation catalyst and the ratio of vinylidene olefins to vinylene olefins in the olefin feed undergoing hydroformylation. By applying the disclosure herein, it may be possible to tailor the branch content and the lubricant and surfactant properties to a greater extent than is achievable through the Guerbet reaction or with other hydroformylation catalysts, such as phosphine-modified cobalt or rhodium catalysts, where tolerance to internal olefins may be reduced. Thus, the present disclosure may afford branched alcohol molecules tailored for specific applications that are currently met inefficiently or are unmet with other alcohols or various reaction products formed therefrom.

All numerical values within the detailed description and the claims herein are modified by "about" or "approximately" with respect to the indicated value, and take into account experimental error and variations that would be expected by a person having ordinary skill in the art. Unless otherwise indicated, room temperature is about 25° C.

As used in the present disclosure and claims, the singular forms "a," "an," and "the" include plural forms unless the context clearly dictates otherwise.

The term "and/or" as used in a phrase such as "A and/or B" herein is intended to include "A and B," "A or B," "A", and "B."

For the purposes of the present disclosure, the new numbering scheme for groups of the Periodic Table is used. In said numbering scheme, the groups (columns) are numbered sequentially from left to right from 1 through 18, excluding the f-block elements (lanthanides and actinides).

The term "hydrocarbon" refers to a class of compounds containing hydrogen bound to carbon, and encompasses (i) saturated hydrocarbon compounds, (ii) unsaturated hydrocarbon compounds, and (iii) mixtures of hydrocarbon compounds (saturated and/or unsaturated), including mixtures of hydrocarbon compounds having different numbers of carbon atoms. The term "$C_n$" refers to hydrocarbon(s) or a hydrocarbyl group having n carbon atom(s) per molecule or group, wherein n is a positive integer. Such hydrocarbons or hydrocarbyl groups may be one or more of linear, branched, cyclic, acyclic, saturated, unsaturated, aliphatic, or aromatic.

The terms "saturated" or "saturated hydrocarbon" refer to a hydrocarbon or hydrocarbyl group in which all carbon atoms are bonded to four other atoms or bonded to three other atoms with one unfilled valence position thereon.

The terms "unsaturated" or "unsaturated hydrocarbon" refer to a hydrocarbon or hydrocarbyl group in which one or more carbon atoms are bonded to less than four other atoms, optionally with one unfilled valence position on the one or more carbon atoms.

The terms "hydrocarbyl" and "hydrocarbyl group" are used interchangeably herein. The term "hydrocarbyl group" refers to any $C_1$-$C_{100}$ hydrocarbon group bearing at least one unfilled valence position when removed from a parent compound. "Hydrocarbyl groups" may be optionally substituted, in which the term "optionally substituted" refers to replacement of at least one hydrogen atom or at least one carbon atom with a heteroatom or heteroatom functional group. Heteroatoms may include, but are not limited to, B, O, N, S, P, F, Cl, Br, I, Si, Pb, Ge, Sn, As, Sb, Se, and Te. Heteroatom functional groups that may be present in substituted hydrocarbyl groups include, but are not limited to, functional groups such as O, S, S=O, S(=O)$_2$, NO$_2$, F, Cl, Br, I, NR$_2$, OR, SeR, TeR, PR$_2$, AsR$_2$, SbR$_2$, SR, BR$_2$, SiR$_3$, GeR$_3$, SnR$_3$, PbR$_3$, where R is a hydrocarbyl group or H. Suitable hydrocarbyl groups may include alkyl, alkenyl, alkynyl, aryl, heteroaryl, cycloalkyl, cycloalkenyl, heterocyclyl, and the like, any of which may be optionally substituted.

The term "alkyl" refers to a hydrocarbyl group having no unsaturated carbon-carbon bonds, and which may be optionally substituted.

The term "alkenyl" refers to a hydrocarbyl group having a carbon-carbon double bond, and which may be optionally substituted. The terms "alkene" and "olefin" may be used synonymously herein. Similarly, the terms "alkenic" and "olefinic" may be used synonymously herein. Unless otherwise noted, all possible geometric and positional isomers are encompassed by these terms.

The terms "aromatic" and "aromatic hydrocarbon" refer to a hydrocarbon or hydrocarbyl group having a cyclic arrangement of conjugated pi-electrons that satisfy the Hückel rule. The term "aryl" is equivalent to the term "aromatic" as defined herein. The term "aryl" refers to both aromatic compounds and heteroaromatic compounds, either of which may be optionally substituted. Both mononuclear and polynuclear aromatic compounds are encompassed by these terms.

Examples of saturated hydrocarbyl groups include, but are not limited to, methyl, ethyl, n-propyl, isopropyl, n-butyl, isobutyl, sec-butyl, tert-butyl, pentyl, isopentyl, hexyl, octyl, cyclopropyl, cyclobutyl, cyclopentyl, cyclohexyl, cyclooctyl, and the like, including their substituted analogues. Examples of unsaturated hydrocarbyl groups include, but are not limited to, ethenyl, propenyl, allyl, butadienyl, cyclopropenyl, cyclobutenyl, cyclopentenyl, cyclohexenyl, cyclooctenyl and the like, including their substituted analogues.

Examples of aromatic hydrocarbyl groups include, but are not limited to, phenyl, tolyl, xylyl, naphthyl, and the like, including all possible isomeric forms thereof. Polynuclear aromatic hydrocarbyl groups may include, but are not limited to, naphthalene, anthracene, indane, and indene.

The terms "oligomer(s)" and "oligomeric product" refer to a molecule having a predetermined number of repeating monomer units, where the number of repeating monomer units is relatively small and specifiable. Illustrative oligomers include dimers, trimers, tetramers, higher oligomers, and mixtures thereof. The term "oligomerization process" refers to any process of catalytically joining monomer units together to form one or more oligomers.

The terms "linear" and "linear hydrocarbon" refer to a hydrocarbon or hydrocarbyl group having a continuous carbon chain without side chain branching, in which the continuous carbon chain may be optionally substituted with heteroatoms or heteroatom groups.

The terms "branch," "branched" and "branched hydrocarbon" refer to a hydrocarbon or hydrocarbyl group having a linear main carbon chain in which a hydrocarbyl side chain extends from the linear main carbon chain. Optional heteroatom substitution may be present in the linear main carbon chain or in the hydrocarbyl side chain.

The term "linear alpha olefin (LAO)" refers to a substantially linear alkenic hydrocarbon bearing a carbon-carbon double bond at a terminal (end) carbon atom of the main carbon chain. LAOs are exemplary alkenic hydrocarbons bearing vinyl group carbon chain termination. The vinyl group bears two hydrogen atoms upon C-1, one hydrogen atom upon C-2 and one hydrocarbyl group upon C-2 of the olefin moiety.

The term "vinylidene" refers to an olefin moiety bearing two hydrogen atoms upon C-1 and two hydrocarbyl groups upon C-2 of the olefin moiety.

The term "disubstituted" refers to an olefin moiety, in which each carbon atom of the double bond bears a single hydrocarbyl group. The double bond geometry in a disubstituted vinylene olefin may be cis or trans.

The term "trisubstituted" refers to an olefin moiety bearing two hydrocarbyl groups upon a first carbon atom of the olefin moiety and one hydrocarbyl group and one hydrogen atom upon a second carbon atom of the olefin moiety, wherein the olefin moiety is non-terminal. Any geometric configuration of the double bond may be present.

The term "vinylene" refers collectively to disubstituted olefins and trisubstituted olefins.

Compositions of the present disclosure comprise alcohol molecules that are formed from a vinylidene olefin via a hydroformylation process. In particular, the vinylidene olefin may be prepared by dimerizing a linear alpha olefin (LAO) or mixture of LAOs. Variable amounts of trisubstituted olefins and/or disubstituted olefins may form concurrently with vinylidene olefins when dimerizing one or more LAOs, and the trisubstituted olefins and disubstituted olefins may similarly form alcohol molecules during the hydroformylation process.

Reaction 1 below illustrates the general structure for a pair of LAOs and their subsequent dimerization to form an LAO dimer comprising a vinylidene group (i.e., a vinylidene olefin). For Reaction 1, $R^1$ and $R^2$ are each an alkyl group having about 6 to about 12 carbon atoms. Each LAO may be of the same length, or they may be of differing lengths. That is, $R^1$ and $R^2$ may be the same or different. If $R^1$ and $R^2$ differ, statistical mixtures of vinylidene olefins having differing numbers of carbon atoms may be obtained. That is, vinylidene olefins comprising $R^1$-$R^1$, $R^2$-$R^2$ or $R^1$-$R^2$ dimers joined to a vinylidene group may be formed. Optional methyl and/or ethyl branching may be present within $R^1$ and/or $R^2$, but such branching is preferably absent. Alpha olefins having one methyl or ethyl branch per molecule in any location will also be considered to constitute linear alpha olefins for purposes of the present disclosure. Carbon atoms within the branches are not included in the total carbon counts of the LAOs employed herein. As such, vinylidene olefins suitable for use in the disclosure herein may be formed from one or more linear alpha olefins and contain about 16 to about 28 carbon atoms, not including any methyl or ethyl branches in $R^1$ or $R^2$.

Reaction 1

The corresponding disubstituted and/or trisubstituted olefin dimers may form as a side product during LAO dimerization, with variable amounts of dimers being formed depending on the particular catalyst and oligomerization conditions used. The formation of disubstituted olefin dimers is shown in Reaction 2A below, and formation of the corresponding trisubstituted olefin dimers is shown in Reaction 2B below, wherein indeterminate olefin geometry in each case is indicated by a wavy bond. $R^1$ and $R^2$ are defined in the same manner as for Reaction 1, and the LAOs undergoing dimerization may be the same or different. Again, optional branching may be present in $R^1$ and/or $R^2$.

Reaction 2A

Reaction 2B

Such vinylene olefin dimers may be removed from the corresponding vinylidene olefins prior to performing hydroformylation according to the disclosure herein, or the vinylene olefin dimers may undergo concurrent hydroformylation as well. Advantageously, a majority of the primary alcohol reaction products formable from trisubstituted olefin dimers may aid in raising the average number of branches formed within the compositions, as discussed further herein.

LAOs, which also may be referred to as terminal olefins or terminal alkenes, may be synthesized by several processes starting from low molecular weight feedstock materials. The two primary processes for synthesizing LAOs are oligomerization of ethylene and byproduct isolation from the Fischer-Tropsch synthesis. LAOs may also be isolated from a petroleum refinery stream. Depending on whether LAOs originate from petroleum or are produced synthetically, a variable extent of branching may be optionally present along the main carbon chain, with such branched olefins still being considered linear alpha olefins. LAOs formed through oligomerization of ethylene, which contain an even number of carbon atoms in homologous series following oligomerization, may be desirable due to the relative ease with which they may be formed.

Illustrative LAOs that may undergo dimerization to form a vinylidene olefin according to the disclosure herein include, for example, 1-octene, 1-nonene, 1-decene, 1-undecene, 1-dodecene, 1-tridecene, 1-tetradecene, or any combination thereof. Preferable LAOs may include 1-octene, 1-decene, 1-dodecene, and 1-tetradecene due to their ready formation via ethylene oligomerization. LAOs having a carbon count below $C_8$ or above $C_{14}$ may similarly be employed to prepare related vinylidene olefins having an even lower or higher molecular weight. Any single LAO or mixture of LAOs may be suitably used to form a vinylidene olefin for further hydroformylation according to the disclosure herein.

The LAO dimer (vinylidene olefin) resulting from Reaction 1 may be alternately characterized below as Structure 1, wherein $R^a$ and $R^b$ are each branched or unbranched alkyl groups having about 6 to about 14 carbon atoms, excluding branches and $R^a$ and $R^b$ may be the same or different. If a single LAO undergoes dimerization to afford a vinylidene olefin, then $R^a$ and $R^b$ differ since two of the carbon atoms are incorporated into the vinylidene group. If different LAOs undergo dimerization, then $R^a$ and $R^b$ may be the same or different.

Structure 1

The corresponding vinylene olefins resulting from Reactions 2A and 2B may be recharacterized as Structures 2A and 2B below, wherein $R^c$ and $R^d$ are each branched or unbranched alkyl groups having about 6 to about 12 carbon atoms, excluding branches and $R^c$ and $R^d$ may be the same or different, and $R^e$ and $R^f$ are each branched or unbranched alkyl groups having about 6 to about 12 carbon atoms, excluding branches and $R^e$ and $R^f$ may be the same or different. The differing carbon counts between $R^a/R^b$ and $R^c/R^d$ and $R^e/R^f$ result from the way the structures are defined compared to those shown in Reactions 1, 2A and 2B.

Structure 2A

Structure 2B

The reaction of one or more LAOs to form a vinylidene olefin, optionally in combination with the corresponding trisubstituted olefin and/or disubstituted olefin, may be promoted by various metallocene catalyst systems. Catalyst systems suitable for oligomerizing LAOs into vinylidene olefins may comprise a metallocene catalyst system such as, for example, bis(cyclopentadienyl)zirconium(IV) dichloride ($Cp_2ZrCl_2$) in combination with a suitable activator. Other non-limiting examples of metallocene catalysts that may be suitable for forming vinylidene olefins include, for example, bis(n-propylcyclopentadienyl) zirconium(IV) dichloride, bis(1-butyl-3-methylcyclopentadienyl) zirconium dichloride, Schwartz's reagent (zirconocene chloride hydride), or rac-dimethylsilyl-bis-(tetrahydroindenyl) zirconium dimethyl, each in combination with a suitable activator such as an alumoxane (e.g., methylalumoxane-MAO) or a non-coordinating anion activator. Still other suitable metallocene catalyst systems that may be used for synthesizing vinylidene olefins and/or trisubstituted olefins may be found in commonly owned U.S. Patent Application Publication 2018/0282359, which is incorporated herein by reference in its entirety.

Suitable alumoxanes for serving as a metallocene catalyst activator may be obtained through partial hydrolysis of an alkylaluminum compound, for example. Non-limiting examples of alumoxanes that may be suitable for use in the disclosure herein include those made, for example, through partial hydrolysis of trimethylaluminum, triethylaluminum, tri(n-propyl)aluminum, tri(isopropyl)aluminum, tri(n-butyl) aluminum, tri(isobutyl)aluminum, tri-(tert-butyl)aluminum, tri(n-pentyl)aluminum, tri(n-hexyl)aluminum, tri(n-octyl) aluminum, and mixtures thereof. MAO may be made through partial hydrolysis of trimethylaluminum.

A non-coordinating anion (NCA) is defined to mean an anion either that does not coordinate to a transition metal center or that does coordinate to a transition metal center, but only weakly. The term NCA is defined to include multicomponent NCA-containing activators, such as N,N-dimethylanilinium tetrakis(pentafluorophenyl)borate and N,N-dimethylanilinium tetrakis(heptafluoronaphthyl)borate, that contain an acidic cationic group and the non-coordinating anion. The term NCA is also defined to include neutral Lewis acids, such as tris(pentafluorophenyl)boron, that can react with a catalyst to form an activated species by abstraction of an anionic group. Typically, NCAs coordinate weakly enough that a neutral Lewis base, such as an olefin, can displace the Lewis base from the metal center and therefore become activated toward oligomerization. Any metal or metalloid that can form a compatible, weakly coordinating complex may be used or contained in the non-coordinating anion. Suitable metals include, but are not limited to, aluminum, gold, and platinum. Suitable metalloids include, but are not limited to, boron, aluminum, phosphorus, and silicon. The term non-coordinating anion includes neutral activators, ionic activators, and Lewis acid activators.

Particularly suitable NCAs may include, for example, N,N-dimethylanilinium tetra(perfluorophenyl)borate, N,N-dimethylanilinium tetrakis(perfluoronaphthyl)borate, N,N-dimethylanilinium tetrakis(perfluorobiphenyl)borate, N,N-dimethylanilinium tetrakis(3,5-bis(trifluoromethyl)phenyl) borate, triphenylcarbenium tetrakis(perfluoronaphthyl) borate, triphenylcarbenium tetrakis(perfluorobiphenyl) borate, triphenylcarbenium tetrakis(3,5-bis(trifluoromethyl) phenyl)borate, triphenylcarbenium tetra(perfluorophenyl) borate, or any combination thereof.

Oligomerization to form a vinylidene olefin and optionally one or more vinylene olefins (disubstituted and/or trisubstituted olefins) in the presence of a metallocene catalyst may be carried out at a temperature ranging from about 30° C. to about 150° C. Suitable residence times in the reactor may range from about 1 hour to about 48 hours. The oligomerization may be carried out under an atmosphere of inert gas, wherein the gas pressure is slightly higher than ambient pressure, in order to preclude air leakage into the reactor. Both batchwise and continuous reaction conditions may be used for synthesizing vinylidene olefins suitable for use in the disclosure herein. For continuous reaction conditions, any of continuously stirred tank reactors, plug flow reactors or loop reactors may be used.

The vinylidene olefins and optional vinylene olefins (disubstituted and/or trisubstituted olefins) discussed above may undergo hydroformylation to form various branched, long-chain primary alcohols following reduction of the hydroformylated reaction product. Depending on the catalyst used to promote the hydroformylation reaction, varying ratios of β-branched to γ-branched primary alcohols may be produced.

Accordingly, compositions of the present disclosure may comprise a mixture comprising reduced hydroformylated reaction products of a vinylidene olefin, in which the reduced hydroformylated reaction products comprise alcohol molecules represented by at least one of Structure 3, Structure 4 and Structure 5.

Structure 3

Structure 4

Structure 5

$R^a$ and $R^b$ are each a branched or unbranched alkyl group having about 6 to about 14 carbon atoms, excluding branches and $R^a$ and $R^b$ may be the same or different. Variable m is an integer ranging from 0 to a number of carbon atoms in $R^b$. $R^{b'}$ is a branched or unbranched alkyl group having m+1 carbon atoms less than $R^b$. The mixture may have an average of about 1.2 to about 2.1 branches per alcohol molecule, or about 1.2 to about 2.0 branches per alcohol molecule, or about 1.7 to about 2.1 branches per alcohol molecule. The average number of branches within this range results from the tendency of the hydroformylation reaction conditions and hydroformylation catalysts herein to form β-branched reduced hydroformylated reaction products competitively with γ-branched reduced hydroformylated reaction products.

When two olefins having different carbon counts undergo dimerization to form the vinylidene olefin, $R^a$ and $R^b$ may be the same or different. When a single olefin undergoes dimerization, $R^a$ and $R^b$ have a different chain length, since two carbon atoms from one of the olefin molecules is incorporated into the vinylidene group.

When vinylene olefins (disubstituted and/or trisubstituted olefins) are present in combination with the vinylidene olefins, the mixture may further comprise one or more reduced hydroformylated reaction products of the vinylene olefins. The one or more reduced hydroformylated reaction products of trisubstituted olefins within the vinylene olefins may comprise alcohol molecules represented by at least one of Structure 6, Structure 7, Structure 8, Structure 9, and Structure 10.

Structure 6

Structure 7

Structure 8

Structure 9

Structure 10

In Structures 6-10, $R^c$ and $R^d$ are each a branched or unbranched alkyl group having about 6 to about 12 carbon atoms, excluding branches and $R^c$ and $R^d$ may be the same or different. Variable n is an integer ranging from 0 to a number of carbon atoms in $R^c$. $R^{c'}$ is a branched or unbranched alkyl group having n+1 carbon atoms less than $R^c$, unless variable n is the same as the number of carbon atoms in $R^c$, excluding branches, in which case $R^{c'}$ is H. Variable o is an integer ranging from 0 to a number of carbon atoms in $R^d$. $R^{d'}$ is a branched or unbranched alkyl group having o+1 carbon atoms less than $R^d$, unless variable o is the same as the number of carbon atoms in $R^d$, excluding branches, in which case $R^{d'}$ is H. All of Structures 6-10, except for Structure 9, contain two branches and supplement the average number of branches within the mixture. It is to be appreciated that alcohol migration all the way to the terminal carbon atom may also occur during hydroformylation in some cases, as shown in Structures 11 and 12, wherein p is an integer ranging from 0 to one more than the number of carbon atoms in $R^c$ and q is an integer ranging from 0 to the number of carbon atoms in $R^d$.

Structure 11

Structure 12

Collectively, the reduced hydroformylated reaction products of the vinylidene olefin, optionally in combination with the reduced hydroformylated reaction products of the tri-substituted olefin, may afford the mixture an average of about 1.2 to about 2.1 branches per alcohol molecule, or about 1.2 to about 2.0 branches per alcohol molecule, or about 1.7 to about 2.1 branches per alcohol molecule. γ-Branched alcohols (Structures 3 and 9) have a single branch per alcohol molecule, whereas β-branched alcohols have two branches per alcohol molecule. Since β-branched alcohols are formed competitively under the catalytic hydroformylation reaction conditions disclosed herein, the average number of branches may be statistically weighted toward a value of 2 (two branches per alcohol molecule), with the actual ratio being dependent upon the composition of the starting olefin feed and the particular hydroformylation conditions used. In contrast, hydroformylation conditions favoring the formation of γ-branched alcohols trend toward a value of 1 (one branch per alcohol molecule), as may occur when using phosphine-modified hydroformylation catalysts, for example. If there are no branches initially present in $R^a$, $R^b$, $R^c$ and/or $R^d$, the mixture has a theoretical maximum number of branches of 2. The higher average number of branches of about 2.1 accounts for the possibility of a limited number of branches residing with $R^a$, $R^b$, $R^c$ and/or $R^d$. In more particular examples, the mixture may feature an average of about 1.8 to about 2.1 branches per alcohol molecule or an average of about 1.9 to about 2.1 branches per alcohol molecule.

As shown above, hydroformylation may introduce a hydroxymethyl group directly to either of the carbon atoms that were formerly double bonded carbon atoms of the vinylidene olefin or the trisubstituted olefin. Alternately, double bond migration may occur under the hydroformylation conditions such that the hydroxymethyl group becomes attached to a carbon atom remote from the former double bonded carbon atoms in the starting material (e.g., Structures 5, 8 and 10-12). It is to be appreciated that variables m, n, o, p and q represent the extent to which the double bond migrates.

As referenced above, the vinylidene olefin is only limited within the bounds defining Structure 1. In more particular examples, the vinylidene olefin may be formed via dimerization of one or more LAOs. Particular vinylidene olefins may comprise about 16 to about 30 carbon atoms or about 18 to about 28 carbon atoms when formed from LAOs, such that the corresponding reduced hydroformylated reaction products comprise about 17 to about 31 carbon atoms or about 19 to about 29 carbon atoms. Certain reduced hydroformylated reaction products of the present disclosure may be formed from a $C_{20}$ vinylidene olefin (e.g., a vinylidene olefin formed through dimerization of 1-decene) and therefore comprise 21 carbon atoms in total, provided that no additional side-chain branching is present.

As shown in Reaction 3 below, vinylidene olefins may be hydroformylated using synthesis gas in the presence of a suitable catalyst to introduce an aldehyde moiety, thereby consuming the olefin moiety and forming one or more hydroformylated reaction products. Reaction 4 shows the corresponding hydroformylation reaction occurring for tri-substituted olefins. Synthesis gas or "syngas," a mixture of carbon monoxide and hydrogen, may be obtained through partial oxidation technology, steam reforming, or a combination thereof. The molar ratio of carbon monoxide to hydrogen may range from about 0.8:1 to about 1.4:1 and may be about 1:1 in particular examples. Although Reactions 3 and 4 have shown the formation of a single β-branched hydroformylated reaction product and the corresponding reduced hydroformylated reaction product, it is to be understood that a mixture of products, including mixtures of β-branched and γ-branched hydroformylated reaction products, may be obtained at each operational stage. Reaction 5 shows the corresponding reaction occurring for disubstituted olefins.

Reaction 3

Reaction 4

Reaction 5

As further shown in Reactions 3-5, the hydroformylated reaction products may undergo subsequent reduction to convert the aldehyde moiety into reduced hydroformylated reaction products containing a primary alcohol. The reduction reaction(s) and any commensurate purification processes (e.g., filtration, drying, distillation, or the like) may be referred to as "finishing" herein. The reduced hydroformylated reaction products may collectively exhibit an average number of branches ranging from about 1.2 to about 2.1 or about 1.2 to about 2.0, or about 1.7 to about 2.1, as discussed above. The reduced hydroformylated reaction products bear one carbon atom more than the vinylidene olefin or the trisubstituted olefins from which they were produced. Reduction may comprise exposing the hydroformylated reaction products to one or more of hydrogen and a hydrogenation catalyst (i.e., catalytic hydrogenation conditions using a catalyst comprising Fe, Co, Ni, Ru, Rh, Pd, Os, Ir, or Pt, preferably supported on an inorganic substrate, and a hydrogen partial pressure of, for example, about 5 MPa to about 20 mPa, and a reaction temperature up to about 180° C.) or a hydride reducing agent, such as sodium borohydride. Catalytic hydrogenation may remove any residual carbon-carbon unsaturation present in the hydroformylated reaction products, as well as reduce at least a portion of the aldehyde moieties into the primary alcohol moiety. Hydride reduction, either conducted alone or in combination with catalytic hydrogenation, may complete the reduction of the aldehyde moieties into the primary alcohol moiety. In particular process configurations, finishing conditions may comprise exposing the hydroformylated reaction products to catalytic hydrogenation followed by a sodium borohydride reduction to produce the reduced hydroformylated reaction products disclosed herein.

Accordingly, hydroformylation methods of the present disclosure may comprise providing an olefin feed comprising a vinylidene olefin represented by Structure 1, contacting the olefin feed with a syngas mixture comprising carbon monoxide and hydrogen in the presence of an unmodified cobalt catalyst to form hydroformylated reaction products of the vinylidene olefin, and reducing the hydroformylated reaction products of the vinylidene olefin to form a mixture comprising reduced hydroformylated reaction products of the vinylidene olefin, in which the reduced hydroformylated reaction products of the vinylidene olefin comprise alcohol molecules represented by at least one of Structure 3, Structure 4, and Structure 5, wherein the variables are defined further above.

The olefin feed may further comprise a disubstituted olefin represented by Structure 2A and/or a trisubstituted olefin represented by Structure 2B, wherein the mixture may further comprise reduced hydroformylated reaction products of the disubstituted olefin and/or the trisubstituted olefin. The reduced hydroformylated reaction products of the trisubstituted olefin may comprise alcohol molecules represented by at least one of Structure 6, Structure 7, Structure 8, Structure 9, and Structure 10, wherein the variables are defined further above.

Suitable catalysts for conducting the hydroformylation reaction upon the vinylidene olefin and/or the vinylene olefin (disubstituted olefin and/or trisubstituted olefin) may be selected such that β-branched alcohols are formed competitively ratio following reduction of the aldehyde moiety. That is, the hydroformylation catalyst may be selected to place the aldehyde moiety in a position such that β-branched alcohols are formed in a sufficient amount to place the number of branches in a range disclosed herein. In the disclosure herein, the β:γ branch ratio may range from about 1:1 to about 10:1, depending on the content of the olefin feed and the particular hydroformylation reaction conditions employed. Particularly suitable hydroformylation catalysts for forming β-branched alcohols competitively with γ-branched alcohols following reduction may comprise an unmodified cobalt catalyst. The term "unmodified" refers to the condition that an ancillary ligand (e.g., phosphine, phosphite, or carbine) is not employed when using the cobalt catalyst.

The unmodified cobalt catalyst may comprise $HCo(CO)_4$, which may be combined directly with the vinylidene olefins and/or vinylene olefins (disubstituted olefins and/or trisubstituted olefins), or the catalyst may be generated in situ. Generation of $HCo(CO)_4$ in situ may take place using $Co_2(CO)_8$, for example. $HCo(CO)_4$ generation from $Co_2(CO)_8$ may take place via reduction followed by acidification of the reduced cobalt intermediate. Other cobalt carbonyls such as $HCo(CO)_3$, $Co(CO)_4$ and $Co_4(CO)_{12}$ may be employed similarly. It is therefore to be appreciated that the presence of $HCo(CO)_4$ may imply the presence of one or more of $Co_2(CO)_8$, $HCo(CO)_3$, $Co(CO)_4$ and $Co_4(CO)_{12}$ in the disclosure herein. Without being limited by theory or mechanism, it is believed that $HCo(CO)_4$ may form from $Co_2(CO)_8$ by a metallo-radical radical pathway and/or heterolytically from an unsaturated cobalt carbonyl. Other suitable unmodified cobalt catalysts may comprise a cobalt (I), cobalt (II) or cobalt (III) salt such as cobalt fluoride, cobalt chloride, cobalt bromide, cobalt iodide, cobalt nitrate, cobalt sulfate, cobalt oxide, cobalt naphthenate, and cobalt carboxylates such as cobalt acetate, dicobalt tetracetate, cobalt stearate, cobalt acetylacetonate, cobalt isobutyrate and cobalt 2-ethylhexanoate.

Promoters may be used in combination with the unmodified cobalt catalyst in some instances to accelerate the rate at which the catalyst is preformed, wherein preforming refers to the formation of $HCo(CO)_4$. Suitable promoters may include, for example, Lewis bases such as pyridines, amines, and alcohols, and metals, such as palladium.

Effective amounts of the unmodified cobalt catalyst for performing hydroformylation may range from about 200 μmol/mol vinylidene olefin to about 3000 μmol/mol vinylidene olefin. The synthesis gas partial pressure in the hydroformylation reaction may range from about 3 MPa to about 40 MPa, or about 5 MPa to about 35 MPa, or about 25 MPa to about 30 MPa, or about 30 MPa to about 35 MPa.

Hydroformylation may be carried out at a temperature ranging from about −20° C. to about 200° C., or from about 25° C. to about 200° C., or from about 30° C. to about 150° C., or from about 0° C. to about 150° C., or from about 0° C. to about 120° C., or from about 0° C. to about 90° C., or from about 0° C. to about 50° C., or less than 85° C. Reaction times under these conditions may range from about 0.5 hours to about 96 hours. Both batchwise and continuous reaction conditions may be employed for synthesizing reduced hydroformylated reaction products according to the disclosure herein. For continuous reaction conditions, any of continuously stirred tank reactors, plug flow reactors or loop reactors may be used.

Solvents or diluents are not necessary when conducting the hydroformylation reaction according to the disclosure herein. When used, suitable solvents or diluents may include, but are not limited to, alkane solvents, polar protic solvents, polar aprotic solvents, chlorinated solvents and aromatic solvents. In a particular example, up to about 10 wt. % water may be added to control byproduct formation under the hydroformylation reaction conditions. Without being bound by theory or mechanism, water may hinder the formation of aldol condensates and other heavy reaction products.

Conversion of the vinylidene olefin to reduced hydroformylated reaction conditions according to the foregoing hydroformylation reaction conditions may afford a mixture comprising about 65 mol. % or greater alcohol molecules. Concurrently, up to about 35 mol. % unfunctionalized saturated hydrocarbons may also be produced. When formed in significant quantities, other reaction byproducts, such as aldol condensates, plus unfunctionalized saturated hydrocarbons may be produced up to about 35 mol. % or up to about 40 mol. %. The unfunctionalized saturated hydrocarbons may remain with the reduced hydroformylated reaction products or be separated therefrom. Separation may comprise, in some instances, at least partially separating the alcohol molecules from the unfunctionalized saturated hydrocarbons by fraction distillation.

Embodiments disclosed herein include:

A. Compositions comprising β-branched long-chain alcohols. The compositions comprise a mixture comprising reduced hydroformylated reaction products of a vinylidene olefin, the reduced hydroformylated reaction products of the vinylidene olefin comprising alcohol molecules represented by at least one of Structure 3, Structure 4 and Structure 5;

Structure 3

Structure 4

Structure 5 wherein the mixture has an average of about 1.2 to about 2.1 branches per alcohol molecule; and wherein $R^a$ and $R^b$ are each a branched or unbranched alkyl group having about 6 to about 14 carbon atoms, excluding branches and $R^a$ and $R^b$ being the same or different, m is an integer ranging from 0 to a number of carbon atoms in $R^b$, and $R^{b'}$ is a branched or unbranched alkyl group having m+1 carbon atoms less than $R^b$.

B. Methods for hydroformylating vinylidene olefins to produce β-branched alcohols. The methods comprise: providing an olefin feed comprising a vinylidene olefin represented by Structure 1;

Structure 1 wherein $R^a$ and $R^b$ are each a branched or unbranched alkyl group having about 6 to about 14 carbon atoms, excluding branches and $R^a$ and $R^b$ being the same or different; contacting the olefin feed with a syngas mixture comprising carbon monoxide and hydrogen in the presence of an unmodified cobalt catalyst to form hydroformylated reaction products of the vinylidene olefin; and reducing the hydroformylated reaction products of the vinylidene olefin to form a mixture comprising reduced hydroformylated reaction products of the vinylidene olefin, the reduced hydroformylated reaction products of the vinylidene olefin comprising alcohol molecules represented by at least one of Structure 3, Structure 4, and Structure 5;

Structure 3

Structure 4

Structure 5 wherein the mixture has an average of about 1.2 to about 2.1 branches per alcohol molecule; and wherein $R^a$ and $R^b$ are each a branched or unbranched alkyl group having about 6 to about 14 carbon atoms, excluding branches and $R^a$ and $R^b$ being the same or different, m is an integer ranging from 0 to a number of carbon atoms in $R^b$, and $R^{b'}$ is a branched or unbranched alkyl group having m+1 carbon atoms less than $R^b$.

Each of embodiments A and B may have one or more of the following additional elements in any combination:

Element 1: wherein $R^a$ and $R^b$ comprise alkyl groups having a different chain length.

Element 2: wherein the mixture further comprises one or more reduced hydroformylated reaction products of a trisubstituted olefin, the one or more reduced hydroformylated reaction products of the trisubstituted olefin comprising alcohol molecules represented by at least one of Structure 6, Structure 7, Structure 8, Structure 9 and Structure 10;

reduced hydroformylated reaction products of the trisubstituted olefin comprising alcohol molecules represented by at least one of Structure 6, Structure 7, Structure 8, Structure 9 or Structure 10;

Structure 6

Structure 7

Structure 8

Structure 9

Structure 10

Structure 6

Structure 7

Structure 8

Structure 9

Structure 10 wherein $R^c$ and $R^d$ are each a branched or unbranched alkyl group having about 6 to about 12 carbon atoms, excluding branches and $R^c$ and $R^d$ being the same or different, n is an integer ranging from 0 to a number of carbon atoms in $R^c$, $R^{c'}$ is a branched or unbranched alkyl group having n+1 carbon atoms less than $R^c$, o is an integer ranging from 0 to a number of carbon atoms in $R^d$, and $R^{d'}$ is a branched or unbranched alkyl group having o+1 carbon atoms less than $R^d$.

Element 3: wherein the mixture has about 1.8 to about 2.1 branches per alcohol molecule.

Element 4: wherein the mixture has about 1.9 to about 2.1 branches per alcohol molecule.

Element 5: wherein the alcohol molecules consist of 21 carbon atoms in total.

Element 6: wherein the composition further comprises one or more unfunctionalized saturated hydrocarbons.

Element 7: wherein the olefin feed further comprises a trisubstituted olefin represented by Structure 2;

Structure 2 wherein $R^c$ and $R^d$ are each a branched or unbranched alkyl group having about 6 to about 12 carbon atoms, excluding branches and $R^c$ and $R^d$ being the same or different; and wherein the mixture further comprises reduced hydroformylated reaction products of the trisubstituted olefin, the wherein n is an integer ranging from 0 to a number of carbon atoms in $R^c$, $R^{c'}$ is a branched or unbranched alkyl group having n+1 carbon atoms less than $R^c$, o is an integer ranging from 0 to a number of carbon atoms in $R^d$, and $R^{d'}$ is a branched or unbranched alkyl group having o+1 carbon atoms less than $R^d$.

Element 8: wherein the unmodified cobalt catalyst comprises $HCo(CO)_4$.

Element 9: wherein the unmodified cobalt catalyst is generated in situ from $Co_2(CO)_8$.

Element 10: wherein reducing the hydroformylated reaction products comprises exposing the hydroformylated reaction products to one or more of hydrogen and a hydrogenation catalyst, or a hydride reducing agent.

Element 11: wherein reducing the hydroformylated reaction products comprises performing catalytic hydrogenation, followed by a hydride reduction.

Element 12: wherein the syngas mixture comprises a carbon monoxide to hydrogen molar ratio ranging from about 0.8:1 to about 1.4:1.

Element 13: wherein the vinylidene olefin is prepared by dimerizing a linear alpha olefin.

Element 14: wherein the linear alpha olefin comprises a $C_8$, $C_{10}$, $C_{12}$, or $C_{14}$ linear alpha olefin, or any combination thereof.

Element 15: wherein dimerizing takes place in the presence of a metallocene catalyst and a catalyst activator.

Element 16: wherein the catalyst activator comprises an alumoxane or a non-coordinating anion.

Element 17: wherein the mixture comprises about 65 mol. % or greater alcohol molecules.

Element 18: wherein the mixture comprises up to about 35 mol. % unfunctionalized saturated hydrocarbons.

Element 19: wherein the method further comprises at least partially separating the alcohol molecules from the unfunctionalized saturated hydrocarbons by fractional distillation.

By way of non-limiting example, exemplary combinations applicable to A include, but are not limited to, 1 and 2; 1 and 3; 1 and 4; 1 and 5; 1 and 6; 1 and 13; 1 and 17; 1, 17 and 18; 2 and 3; 2 and 4; 2 and 5; 2 and 6; 2 and 13; 2 and 17; 2, 17 and 18; 3 or 4 and 5; 3 or 4 and 6; 3 or 4 and 13; 3 or 4 and 17; 3 or 4 and 17 and 18; 6 and 13; 6 and 17; 6, 17 and 18; 13 and 17; 13, 17 and 18; and 17 and 18. By way of further non-limiting example, exemplary combinations applicable to B include, but are not limited to, 1 and 2; 1 and 3; 1 and 4; 1 and 5; 1 and 6; 1 and 13; 1 and 17; 1, 17 and 18; 2 and 3; 2 and 4; 2 and 5; 2 and 6; 2 and 13; 2 and 17; 2, 17 and 18; 3 or 4 and 5; 3 or 4 and 6; 3 or 4 and 13; 3 or 4 and 17; 3 or 4 and 17 and 18; 6 and 13; 6 and 17; 6, 17 and 18; 13 and 17; 13, 17 and 18; and 17 and 18, any of which may be in further combination with any one or more of elements 7-12 and/or 17-19. Additional exemplary combinations applicable to B include, but are not limited to, 7 and 8; 7-9; 7 and 10; 7 and 11; 7 and 17; 8 and 9; 8 and 10; 8 and 11; 8 and 17; 9 and 10; 9 and 11; 9 and 17; 10 and 17; 10, 17 and 18; 10 and 17-19; 11 and 17; 11, 17 and 18; 11 and 17-19; 7, 13 and 14; 7 and 13-15; 7 and 17; 7, 17 and 18; 7 and 17-19.

To facilitate a better understanding of the embodiments described herein, the following examples of various representative embodiments are given. In no way should the following examples be read to limit, or to define, the scope of the present disclosure.

EXAMPLES

Vinylidene olefin feeds prepared by metallocene-catalyzed dimerization of 1-decene and having compositions as specified in Table 1 were provided.

TABLE 1

| Entry | Overall Feed Composition | | Isomer Composition of $C_{20}$ Dimer | | | |
|---|---|---|---|---|---|---|
| | % Dimer | % Saturates | % Vinylidene | % Vinylene | % Vinyl | % Other |
| E1 | >99 | <1 | >99 | <1 | 1 | — |
| E2 | >99 | 52.7 | 94.2 | 3.1 | 2.4 | 0.3 |

$^1$H and $^{13}$C NMR quantitative analyses were performed to determine the compositions of the finished hydroformylation products described in the examples below.

$^{13}$C NMR quantitative analyses were conducted by dissolving ~200 mg of sample in 3 mL CDCl$_3$ along with 50 mM Cr(acac)$_3$ solution in a 10 mm NMR tube. Data was collected with a cyroprobe on a 600 MHz instrument at 25° C. with inverse gated decoupling over 512 scans with a 90° pulse width, a 60 second delay between scans, and a 200 ppm spectral width. Resonances corresponding to the chain end carbon atoms were assigned a value of 14.10 ppm, and other peaks were referenced with respect to this peak.

$^1$H NMR quantitative analyses were conducted by dissolving ~20-30 mg of sample in 1 mL CDCl$_3$. Data was collected on a 500 MHz instrument at 25° C. over 512 scans with a 30° pulse width, a 5 second delay between scans, and a 20 ppm spectral width. Peaks were referenced to non-deuterated solvent at 7.26 ppm.

General Hydroformylation Conditions: A high-pressure, C-276 alloy autoclave reactor (250 mL) fitted with an interior glass liner and equipped with supervisory control and data acquisition capabilities was utilized to conduct the hydroformylation reaction. In a typical run, a vinylidene olefin feed (130 mL) was introduced to the reactor through an air-free injection port connected to a feed storage vessel. Agitation was initiated, and the reactor was brought to the specified process temperature and a syngas pressure 100 psig (1:1 H$_2$:CO) less than the specified process pressure. The reaction mixture was then allowed to stir for 10 min. to equilibrate. A solution of 20 mL of the specified catalyst in diluent comprising the vinylidene olefin feed was then delivered through an injection port on the autoclave reactor. Syngas was utilized to promote the catalyst injection while simultaneously bringing the unit to the specified process pressure. The process pressure was then maintained throughout the reaction and metered through a mass flow controller. At the end of the run, the syngas supply was halted, and the autoclave reactor was depressurized and purged with nitrogen. Once cool, the autoclave reactor was opened and the liquid product was transferred to a sample container for off-line analyses. Further reaction processing conditions are specified below.

General Hydrogenation Conditions: A high-pressure, C-276 alloy autoclave reactor (250 mL) fitted with an interior glass liner and equipped with supervisory control and data acquisition capabilities was utilized to conduct the hydrogenation experiments. Air-free catalyst handling and injection protocols were similar to the protocols used for hydroformylation experiments. Further reaction processing conditions are specified below.

Example 1: Hydroformylation of Feed E1. Co$_2$(CO)$_8$ (0.261 g, 0.7 mmol) was combined with 91 g of feed E1 (substantially vinylidene olefin). The resulting reaction mixture was injected into a stirred autoclave at 150° C. and charged with 1500 psig of syngas (1:1 H$_2$:CO). The pressure was maintained at 1500 psig for 7 hours at 150° C., and the reaction mixture was then cooled to room temperature and filtered through a packed column of 1:1 (vol./vol.) alumina/silica gel. The resulting pale yellow liquid contained a mixture of aldehydes, alcohols, residual unsaturation, and heavy residues, as analyzed by $^1$H NMR and GC-MS.

The resulting mixture was catalytically hydrogenated by exposure to 0.54 g PtO$_2$ and 2500 psig H$_2$ at 90° C. in the absence of solvent. Following hydrogenation, the product was a colorless liquid. The colorless liquid was then combined with NaBH$_4$ (2.0 g, 0.53 mmol) in 100 mL of tetrahydrofuran (THF) and heated at reflux for 48 hours. After heating, the reaction mixture was combined with 200 mL of isohexane and quenched with 4 M aqueous NH$_4$Cl until a pH of ~8 was reached. After layer separation, the organic phase was dried with Na$_2$SO$_4$ and filtered through silica gel. Following rotary evaporation, a yield of 8.1 g of finished product was obtained. Product characterization is provided below.

Example 2: Hydroformylation of Feed E2. Co$_2$(CO)$_8$ (0.261 g, 0.7 mmol) was combined with 91 g of feed E2 (olefinic mixture comprising vinylidene olefins, disubstituted vinylidene olefins and trisubstituted vinylidene olefins). The resulting reaction mixture was injected into a stirred autoclave at 150° C. and charged with 1500 psig of syngas (1:1 H$_2$:CO). The pressure was maintained at 1500 psig for 7 hours at 150° C., and the reaction mixture was then cooled to room temperature and filtered through a packed column of 1:1 (vol./vol.) alumina/silica gel. The resulting pale yellow liquid contained a mixture of aldehydes, alcohols, residual unsaturation, and heavy residues, as analyzed by $^1$H NMR and GC-MS.

The resulting mixture was catalytically hydrogenated by exposure to 0.54 g PtO$_2$ and 2500 psig H$_2$ at 90° C. in the absence of solvent. Following hydrogenation, the product was a colorless liquid. The colorless liquid was then combined with NaBH$_4$ (2.0 g, 0.53 mmol) in 100 mL of tetrahydrofuran (THF) and heated at reflux for 48 hours. After heating, the reaction mixture was combined with 200 mL of isohexane and quenched with 4 M aqueous NH$_4$Cl until a pH of ~8 was reached. After layer separation, the organic phase was dried with Na$_2$SO$_4$ and filtered through silica gel. Following rotary evaporation, a yield of 39.80 g of finished product was obtained.

Figure 1:
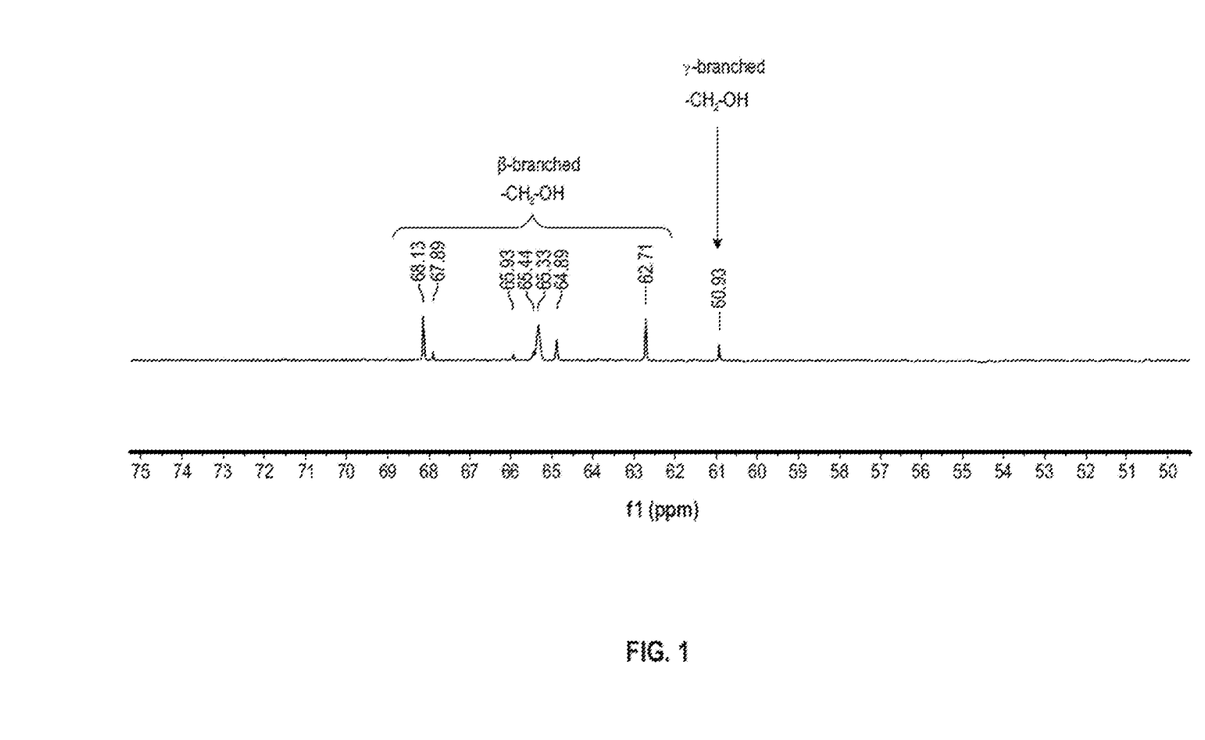
FIG. 1 shows an illustrative $^{13}C$ NMR spectrum of the pre-distillation finished product derived from feed E2 of Example 2 in $C_6D_6$.

Characterization. FIG. 1 shows an illustrative $^{13}$C NMR of the finished product derived from feed E2 (pre-distillation) in C$_6$D$_6$, showing that a range of γ-branched and β-branched long-chain alcohols were produced. Seven resonances corresponding to β-branched long-chain alcohols were observed, indicating that rearrangement occurred during the hydroformylation reaction. A single resonance corresponding to a γ-branched long-chain alcohol was present.

NMR compositional analysis of the hydroformylation products derived from feed E2 is specified in Table 2 and 3 below, respectively.

TABLE 2

|  | Mol. % |
|---|---|
| Total unfunctionalized saturates | 31.0% |
| Total alcohols | 69.0% |
| γ-branched alcohols | 13.6% |
| Tertiary carbon β-branched alcohols | 86.4% |
| Quaternary carbon β-branched alcohols | <1.0% |
| Average branches per alcohol molecule | 1.86 |

Kinematic viscosity was determined at 40° C. (Kv40) or 100° C. (Kv100) using ASTM D445 for the hydroformylation reaction products derived from feed E2. Viscosity index values were determined in accordance with ASTM D2270. Table 3 below summarizes the kinematic viscosity of the finished E2 hydroformylation reaction products in comparison to the starting E2 olefin feed (Standard 1) and a >97% pure γ-branched long-chain alcohol having the same number of carbon atoms (Standard 2).

TABLE 3

| Sample Description | Kv40 (Cs) | Kv100 (Cs) | Viscosity Index |
|---|---|---|---|
| Standard 1 | 1.660 | 4.375 | 177.006 |
| Standard 2 | 4.35 | 34.2 | −60.7 |
| Finished Product Derived from E2 | 4.337 | 25.660 | 54.457 |

The higher kinematic viscosity of the finished product derived from feed E2 relative to Standard 1 is consistent with hydrogen bonding resulting from the introduction of alcohol hydroxyl groups.

Example 3: Product Enrichment. The long-chain alcohols obtained from hydroformylation and subsequent reduction may be substantially enriched by vacuum distillation (200 mtorr) over a temperature range of 150-155° C. at the distillation head. Table 5 below shows a comparison of the finished product composition derived from feed E2 as determined by GC-MS before and after distillation.

TABLE 5

| Product Component | Pre-Distillation Mol. % | Post-Distillation Mol. % |
|---|---|---|
| C$_{20}$ unfunctionalized saturates | 17.9 | 3.1 |
| C$_{21}$ unfunctionalized saturates | 13.1 | 13.2 |
| C$_{21}$ γ- and β-branched alcohols | 69.0 | 82.5 |
| Other | 0 | 1.2 |

As conducted, vacuum distillation affected significant enrichment of the γ- and β-branched alcohols but did not afford complete removal of unfunctionalized saturates. Prolonged heating at elevated temperatures may promote dehydration to form a small amount of C$_{42}$ ethers by a Williamson synthesis route.

Figure 2:
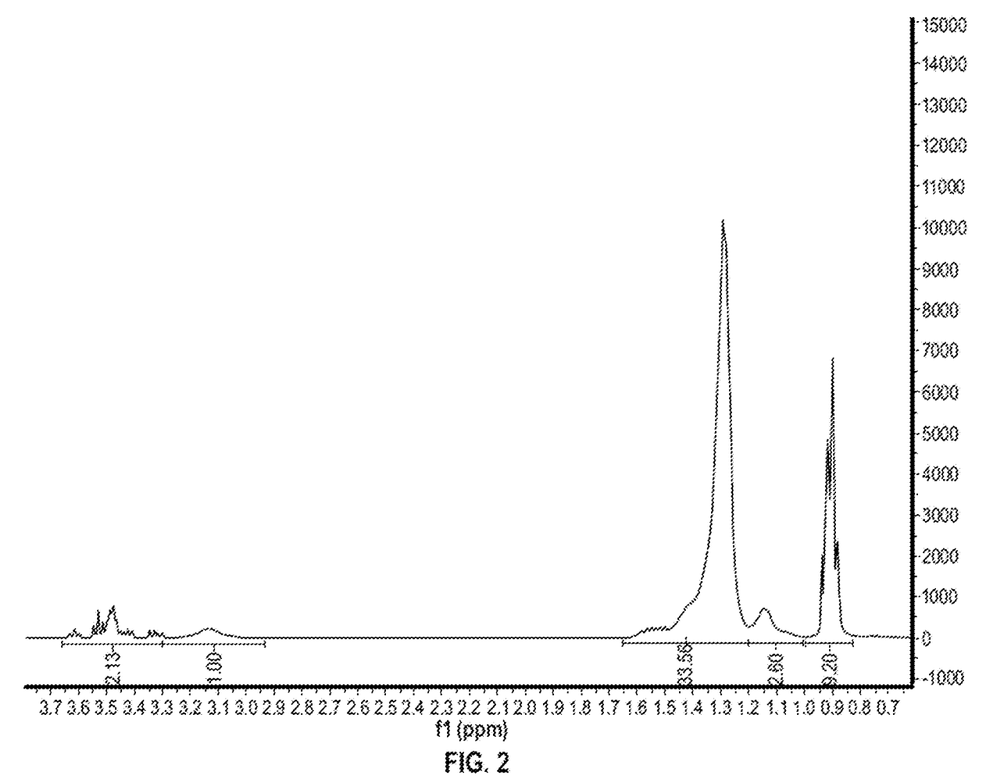
FIG. 2 shows an illustrative $^1H$ NMR spectrum of the finished product derived from feed E2 of Example 2 in $C_6D_6$ following vacuum distillation.
Figure 3:
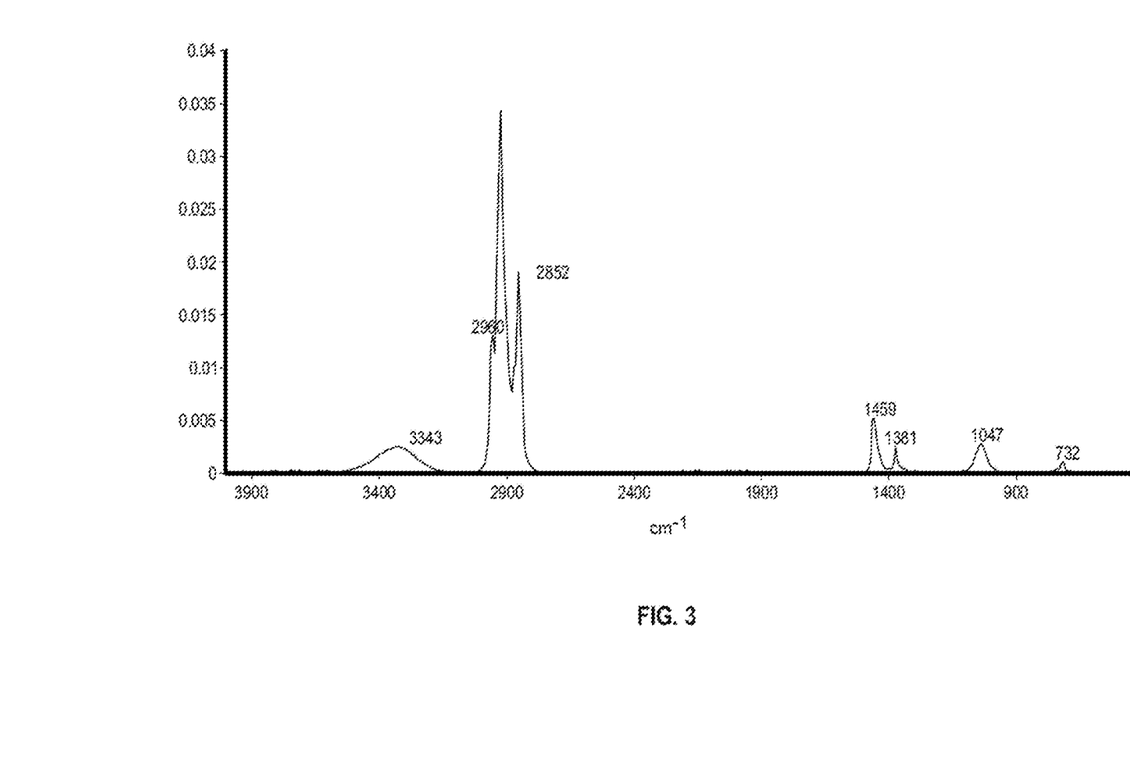
FIG. 3 shows an ATR-IR spectrum of the finished product derived from feed E2 of Example 2 following vacuum distillation.

FIG. 2 shows a $^1$H NMR spectrum of the finished product derived from feed E2 in C$_6$D$_6$ following vacuum distillation. FIG. 3 shows an ATR-IR spectrum of the finished product derived from feed E2 following vacuum distillation. Both spectra were consistent with the presence of alcohol functional groups.

All documents described herein are incorporated by reference herein for purposes of all jurisdictions where such practice is allowed, including any priority documents and/or testing procedures to the extent they are not inconsistent with this text. As is apparent from the foregoing general description and the specific embodiments, while forms of the disclosure have been illustrated and described, various modifications can be made without departing from the spirit and scope of the disclosure. Accordingly, it is not intended that the disclosure be limited thereby. For example, the compositions described herein may be free of any component, or composition not expressly recited or disclosed herein. Any method may lack any step not recited or disclosed herein. Likewise, the term "comprising" is considered synonymous with the term "including." Whenever a method, composition, element or group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least, and not as an attempt to limit the application of the doctrine of equivalents to the scope of the claim, each numerical parameter should at least be construed in light of the number of reported significant digits and by applying ordinary rounding techniques.

Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee.

Moreover, the indefinite articles "a" or "an," as used in the claims, are defined herein to mean one or more than one of the element that it introduces.

One or more illustrative embodiments are presented herein. Not all features of a physical implementation are described or shown in this application for the sake of clarity. It is understood that in the development of a physical embodiment of the present disclosure, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for one of ordinary skill in the art and having benefit of this disclosure.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to one having ordinary skill in the art and having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present disclosure. The embodiments illustratively disclosed herein suitably may be practiced in the absence of any element that is not specifically disclosed herein and/or any optional element disclosed herein.

What is claimed is the following:

1. A composition comprising:
   a mixture comprising reduced hydroformylated reaction products of a vinylidene olefin, the reduced hydroformylated reaction products of the vinylidene olefin comprising alcohol molecules represented by at least one of Structure 3, Structure 4, or Structure 5;

Structure 3

Structure 4

Structure 5 wherein the mixture has an average of about 1.2 to about 2.1 branches per alcohol molecule; and
wherein $R^a$ and $R^b$ are each a branched or unbranched alkyl group having about 6 to about 14 carbon atoms, excluding branches and $R^a$ and $R^b$ being the same or different, m is an integer ranging from 0 to a number of carbon atoms in $R^b$, and $R^{b'}$ is a branched or unbranched alkyl group having m+1 carbon atoms less than $R^b$.

2. The composition of claim 1, wherein $R^a$ and $R^b$ comprise alkyl groups having a different chain length.

3. The composition of claim 1, wherein the mixture further comprises one or more reduced hydroformylated reaction products of a trisubstituted olefin, the one or more reduced hydroformylated reaction products of the trisubstituted olefin comprising alcohol molecules represented by at least one of Structure 6, Structure 7, Structure 8, Structure 9, or Structure 10;

Structure 6

Structure 7

Structure 8

Structure 9

Structure 10 wherein $R^c$ and $R^d$ are each a branched or unbranched alkyl group having about 6 to about 12 carbon atoms, excluding branches and $R^c$ and $R^d$ being the same or different, n is an integer ranging from 0 to a number of carbon atoms in $R^c$, $R^{c'}$ is a branched or unbranched alkyl group having n+1 carbon atoms less than $R^c$, o is an integer ranging from 0 to a number of carbon atoms in $R^d$, and $R^{d'}$ is a branched or unbranched alkyl group having o+1 carbon atoms less than $R^d$.

4. The composition of claim 1, wherein the mixture has about 1.8 to about 2.1 branches per alcohol molecule.

5. The composition of claim 1, wherein the mixture has about 1.9 to about 2.1 branches per alcohol molecule.

6. The composition of claim 1, wherein the alcohol molecules consist of 21 carbon atoms in total.

7. The composition of claim 1, further comprising:
   one or more unfunctionalized saturated hydrocarbons.

8. A method comprising:
   providing an olefin feed comprising a vinylidene olefin represented by Structure 1;

Structure 1 wherein $R^a$ and $R^b$ are each a branched or unbranched alkyl group having about 6 to about 14 carbon atoms, excluding branches and $R^a$ and $R^b$ being the same or different;

contacting the olefin feed with a syngas mixture comprising carbon monoxide and hydrogen in the presence of an unmodified cobalt catalyst to form hydroformylated reaction products of the vinylidene olefin; and reducing the hydroformylated reaction products of the vinylidene olefin to form a mixture comprising reduced hydroformylated reaction products of the vinylidene olefin, the reduced hydroformylated reaction products of the vinylidene olefin comprising alcohol molecules represented by at least one of Structure 3, Structure 4, or Structure 5;

Structure 3

Structure 4

Structure 5 wherein the mixture has an average of about 1.2 to about 2.1 branches per alcohol molecule; and wherein $R^a$ and $R^b$ are each a branched or unbranched alkyl group having about 6 to about 14 carbon atoms, excluding branches and $R^a$ and $R^b$ being the same or different, m is an integer ranging from 0 to a number of carbon atoms in $R^b$, and $R^{b'}$ is a branched or unbranched alkyl group having m+1 carbon atoms less than $R^b$.

9. The method of claim 8, wherein $R^a$ and $R^b$ comprise alkyl groups having a different chain length.

10. The method of claim 8, wherein the olefin feed further comprises a trisubstituted olefin represented by Structure 2;

Structure 2 wherein $R^c$ and $R^d$ are each a branched or unbranched alkyl group having about 6 to about 12 carbon atoms, excluding branches and $R^c$ and $R^d$ being the same or different; and wherein the mixture further comprises reduced hydroformylated reaction products of the trisubstituted olefin, the reduced hydroformylated reaction products of the trisubstituted olefin comprising alcohol molecules represented by at least one of Structure 6, Structure 7, Structure 8, Structure 9, or Structure 10;

Structure 6

Structure 7

Structure 8

Structure 9

Structure 10 wherein n is an integer ranging from 0 to a number of carbon atoms in $R^c$, $R^{c'}$ is a branched or unbranched alkyl group having n+1 carbon atoms less than $R^c$, o is an integer ranging from 0 to a number of carbon atoms in $R^d$, and $R^{d'}$ is a branched or unbranched alkyl group having o+1 carbon atoms less than $R^d$.

11. The method of claim 8, wherein the unmodified cobalt catalyst comprises $HCo(CO)_4$.

12. The method of claim 8, wherein the unmodified cobalt catalyst is generated in situ from $Co_2(CO)_8$.

13. The method of claim 8, wherein reducing the hydroformylated reaction products comprises exposing the hydroformylated reaction products to one or more of hydrogen and a hydrogenation catalyst, or a hydride reducing agent.

14. The method of claim 8, wherein reducing the hydroformylated reaction products comprises performing catalytic hydrogenation, followed by a hydride reduction.

15. The method of claim 8, wherein the syngas mixture comprises a carbon monoxide to hydrogen molar ratio ranging from about 0.8:1 to about 1.4:1.

16. The method of claim 8, wherein the mixture has about 1.8 to about 2.1 branches per alcohol molecule.

17. The method of claim 8, wherein the mixture has about 1.9 to about 2.1 branches per alcohol molecule.

18. The method of claim 8, wherein the alcohol molecules consist of 21 carbon atoms in total.

19. The method of claim 8, wherein the vinylidene olefin is prepared by dimerizing a linear alpha olefin.

20. The method of claim 19, wherein the linear alpha olefin comprises a $C_8$, $C_{10}$, $C_{12}$, or $C_{14}$ linear alpha olefin, or any combination thereof.

21. The method of claim 19, wherein dimerizing takes place in the presence of a metallocene catalyst and a catalyst activator.

22. The method of claim 21, wherein the catalyst activator comprises an alumoxane or a non-coordinating anion.

23. The method of claim 8, wherein the mixture comprises about 65 mol. % or greater alcohol molecules.

24. The method of claim 8, wherein the mixture comprises up to about 35 mol. % unfunctionalized saturated hydrocarbons.

25. The method of claim 24, further comprising:
- at least partially separating the alcohol molecules from the unfunctionalized saturated hydrocarbons by fractional distillation.

* * * * *